United States Patent
Sela (10) Patent No.: US 10,092,206 B2
(45) Date of Patent: Oct. 9, 2018

(54) NEUROFEEDBACK TREATMENT SYSTEM AND METHOD

(71) Applicant: Rivka Sela, Shoham (IL)

(72) Inventor: Rivka Sela, Shoham (IL)

( * ) Notice: Subject to any disclaimer, the term of this patent is extended or adjusted under 35 U.S.C. 154(b) by 666 days.

(21) Appl. No.: 14/048,455

(22) Filed: Oct. 8, 2013

(65) Prior Publication Data

US 2014/0163410 A1   Jun. 12, 2014

Related U.S. Application Data

(60) Provisional application No. 61/734,374, filed on Dec. 7, 2012.

(51) Int. Cl.
*A61B 5/0482* (2006.01)
*A61B 5/00* (2006.01)
*A61B 5/0478* (2006.01)

(52) U.S. Cl.
CPC .......... *A61B 5/0482* (2013.01); *A61B 5/0006* (2013.01); *A61B 5/0478* (2013.01); *A61B 5/6803* (2013.01)

(58) Field of Classification Search
None
See application file for complete search history.

(56) References Cited

U.S. PATENT DOCUMENTS

| | | |
|---|---|---|
| 5,377,100 A | 12/1994 | Pope et al. |
| 5,899,867 A | 5/1999 | Collura |
| 6,097,980 A | 8/2000 | Monastra et al. |
| 6,450,820 B1 | 9/2002 | Palsson et al. |
| 6,574,513 B1 | 6/2003 | Collura et al. |
| 7,150,715 B2 | 12/2006 | Collura et al. |
| 7,269,456 B2 | 9/2007 | Collura |
| 8,005,691 B2 | 8/2011 | Kumar et al. |
| 8,311,622 B2 | 11/2012 | Snyder et al. |
| 2002/0028988 A1* | 3/2002 | Suzuki .............. A61B 5/0002 600/300 |
| 2002/0120208 A1* | 8/2002 | Kim .................. A61B 5/0482 600/545 |
| 2002/0198473 A1* | 12/2002 | Kumar ................ A61N 1/08 600/595 |
| 2004/0133119 A1* | 7/2004 | Osorio ............... A61B 5/048 600/544 |

(Continued)

OTHER PUBLICATIONS

"BioEra = Visual Designer for Biofeedback" Oct. 20, 2012 https://web.archive.org/web/20121030205155/http://www.bioera.net/index.shtml.*

(Continued)

*Primary Examiner* — Jacqueline Cheng
*Assistant Examiner* — Jairo Portillo
(74) *Attorney, Agent, or Firm* — Mark David Torche; Patwrite Law (57) ABSTRACT

A neurofeedback system for providing neurofeedback to at least one patient. The neurofeedback system includes: EEG head sensors; a central server to store treatment protocol algorithm(s) provided via the Internet; and a data collection module associated with a computer-based device. The data collection module: transmits the EEG brain activity to the central server via the Internet by way of the computer-based device; provides feedback to the patient; and receives a treatment protocol from the central server via the Internet by way of the computer-based device.

18 Claims, 2 Drawing Sheets

(56) References Cited

U.S. PATENT DOCUMENTS

| | | |
|---|---|---|
| 2008/0177197 A1 | 7/2008 | Lee et al. |
| 2009/0069707 A1* | 3/2009 | Sandford ............... A61B 5/165 |
| | | 600/545 |
| 2010/0016753 A1* | 1/2010 | Firlik .................. A61B 5/0006 |
| | | 600/545 |
| 2010/0094156 A1 | 4/2010 | Collura |
| 2013/0066183 A1 | 3/2013 | Jin et al. |

OTHER PUBLICATIONS

"Brainmaster Technologies, Inc." Jul. 12, 2012 https://web.archive.org/web/20120712192842/http://store.brainmaster.com:80/.*

Martin, George, and Cynthia L. Johnson. "The boys Totem town neurofeedback project: A pilot study of EEG biofeedback with incarcerated juvenile felons." Journal of Neurotherapy 9.3 (2006): 71-86.*

* cited by examiner

NEUROFEEDBACK TREATMENT SYSTEM AND METHOD

CROSS REFERENCE TO RELATED APPLICATIONS

This application claims priority from provisional patent application U.S. 61/734,374, entitled NEUROFEEDBACK TREATMENT SYSTEM, filed on Dec. 7, 2012, the entire contents of which is incorporated herein by reference.

FIELD OF THE INVENTION

The present invention relates to neurotherapy, and more particularly to a system and method for performing neurofeedback treatment.

BACKGROUND OF THE INVENTION

Neurofeedback is a non-invasive treatment method whose purpose is to change the electrical activity of the brain. The method is safe and has been proposed for treating a range of neuropsychiatric disorders, such as epilepsy and ADHD. The method is based on giving real-time feedback to the patient based on the electric activity (EEG) of the brain to train and condition the patient's brain.

The neurofeedback treatment system commonly uses a video that the patient views or an inter-active computer console-type game that the patient plays. The real-time feedback to the patient typically includes one or a combination of a visual feedback (i.e. affecting the view on the screen, for example, dimming, blurring, decreasing the size and so on, or audio feedback (for example, a message or beeping signal). Electrodes appropriately placed on the patient's head measure the brain activity to determine if the patient is concentrating above a controllable threshold or not while watching the video or playing the video game. If less than an acceptable level of brain activity is detected, the system will then cause the screen to provide the (negative) real-time feedback as aforementioned.

In the last decade, with the progress of research and technology in the field, the number of therapists who practice neurotherapy has increased. Regardless, because of the high cost of the treatment due to factors such as the high equipment cost, costly therapist time; and the low availability of therapists, the treatment is not as common as would be expected for a safe treatment that represents an effective alternative to medication.

The following publications are believed to represent the current state of the art: U.S. Pat. No. 8,311,622 (Snyder et al., Nov. 13, 2012); U.S. Pat. No. 8,005,691 (Kumar et al., Aug. 23, 2011); U.S. Pat. No. 7,269,456 (Collura, Sep. 11, 2007); U.S. Pat. No. 7,150,715 (Collura et al., Dec. 19, 2006); U.S. Pat. No. 6,574,513 (Collura et al, Jun. 3, 2003); U.S. Pat. No. 6,450,820 (Palsson et al., Sep. 17, 2002); U.S. Pat. No. 6,097,980 (Monastra et al., Aug. 1, 2000); U.S. Pat. No. 5,899,867 (Collura, May 4, 1999); U.S. Pat. No. 5,377,100 (Pope et al., Dec. 27, 1994); US 2013/066183 (Jin et al., Mar. 14, 2013); US 2010/094156 (Collura, Apr. 15, 2010); US 2010/016753 (Firlik, Jan. 21, 2010); and US2008/177197 (Lee et al., Jul. 24, 2008), all of which are incorporated herein by reference.

US 2010/016753 (Frilik) is entitled "Systems and Methods for Portable Neurofeedback" discloses a neurofeedback system including a portable device for receiving, processing and displaying brain electrical activity in real-time. The portable device may be, for example, a Personal Digital Assistant (PDA), a cell phone or smartphone, for example an iPhone®, an N-Gage and a Blackberry®; a handheld gaming device, for example a Nintendo Game Boy, a Nintendo DS, a POSBRO G100 Mobile WiMAX, Sony PlayStation Portable, or similar electronic devices; a computer, for example a laptop; and a netbook. The brain electrical activity is provided visually on the portable device as visual feedback. The system also includes sensors for capturing, recording and transmitting the brain electrical activity.

SUMMARY OF THE INVENTION

The present invention relates to a neurofeedback system and method for using the system. The present improved neurofeedback system and method is adapted to allow for convenient home use, or use outside the home, meaning the user/patient need not be in a neurofeedback clinic to use the system/method.

It is a particular feature of the present system and method that they are adapted to perform an automatic or semi-automatic neurofeedback treatment. The adaptation includes that the system can automatically make a neurofeedback treatment protocol. If the treatment is implemented in an automatic manner, it is another particular feature of the present system and method that they are adapted to automatically provide a treatment protocol by use of a built-in or downloadable/insertable algorithm either pre-determined or chosen by the therapist.

In this regard, it is another particular feature of the present system and method that they are adapted whereby a therapist, or the system itself, can provide a treatment plan or so-called "protocol" remotely. Note, this is not the same as a patient being able to choose what issue to work on (e.g. ADHD, phobia, etc.) or at what difficulty level. The point is the protocol or treatment plan can be designed by a therapist when the patient is not at a clinic and also implemented when the patient is not in a clinic.

It is another particular feature of the present system and method that they are adapted to perform when provided via a wide variety of commonly used computer-based programs/activities, i.e. that are in every day use of the patient, for example: word processing programs, spreadsheet programs (e.g. Excel); PowerPoint; video-sharing programs/sites (e.g. YouTube); social networking programs (e.g. Facebook, Google+, LinkedIn, MYSpace, Twitter) on-line games; email; Internet surfing; and so on; and not merely provided on various devices. In other words, computer-based programs/activities of the type beyond merely videos and video games, which are presently used.

In the present description and claims, the term "computer-based programs/activities" will denote programs and activities such as those listed above and which are specifically not videos or computer console-type games. Regardless, the instant invention can be used with computer-operated videos and on-line computer games.

The term "computer-based programs/activities", and its derivatives, will be used herein the specification and claims to include the previously mentioned programs/activities.

The term "computer-based device", and its derivatives, will be used herein the specification and claims to include a desk-top computer; a laptop computer; a Personal Digital Assistant (PDA); a cell phone/smart phone (e.g. iPhone®; Blackberry®); or similar devices that are Internet/cloud connectable.

In accordance with embodiments of one aspect of the present invention there is provided a neurofeedback system for providing neurofeedback to at least one patient. The neurofeedback system includes (a) sensors attachable to the head of the at least one patient and configured to measure electroencephalographic brain activity of the at least one patient; (b) a central server configured to store at least one treatment protocol algorithm whereby the central server provides said treatment protocol via the Internet in accordance with the measured electroencephalographic brain activity (i.e. quality/level of the activity); and (c) at least one data collection module operably/communicatively respectively associated with a computer-based device, which is capable of accessing the Internet and capable of providing at least one computer-based program/activity. The data collection module is configured to: (i) transmit the measured electroencephalographic brain activity to said central server via the Internet by way of the computer-based device; (ii) provide feedback to the at least one patient in accordance with the measured electroencephalographic brain activity; and (iii) receive a treatment protocol from the central server via the Internet by way of the computer-based device.

According to some embodiments, the system further includes at least one therapist interface for respectively interfacing with at least one therapist and interfacing with the Internet to thereby receive the electroencephalographic brain activity data measured by said set of sensors associated with the at least one patient.

According to some embodiments, the system further includes a clinic server configured to interface with the Internet.

According to some embodiments, the central server is configured to automatically provide treatment protocols based on the electroencephalographic brain activity whereby continued neurofeedback treatments can be performed without monitoring by a therapist.

According to some embodiments, the at least one computer-based program/activity comprises any one or combination of: a word processing program, a spreadsheet program; a presentation program; a social networking program; an on-line game; e-mail; Internet surfing; and a video-sharing program/site.

According to some embodiments, the computer-based device includes any one or combination of a desk-top computer; a laptop computer; a Personal Digital Assistant; a cellphone/smartphone; and a computer operated gaming device.

According to some embodiments, the system includes a plurality of data collection modules whereby a plurality of patients can simultaneously use the system.

According to some embodiments, the system further includes a treatment package purchase module for allowing an organization to purchase use of the system.

According to some embodiments, the system further includes a patient treatment purchase module for allowing at least one patient to purchase one or more neurofeedback treatments.

According to some embodiments, the treatment protocol received via the Internet includes at least one subsequent treatment protocol in accordance with progress of the at least one patient.

According to some embodiments, the feedback to each patient is an audio feedback. According to some embodiments, the feedback to each patient is a visual feedback.

According to some embodiments, the sensors are part of a portable head-set.

In accordance with embodiments of another aspect of the present invention there is provided a method of providing neurofeedback treatment to at least one patient. The method includes (a) securing electrodes to the head of the at least one patient, the electrodes configured to measure electroencephalographic brain activity; (b) providing a central server configured to store at least one treatment protocol algorithm whereby the central server provides said treatment protocol via the Internet in accordance with the measured electroencephalographic brain activity (i.e. quality/level of the activity); (c) installing at least one data collection module operably/communicatively in a computer-based device, which is capable of accessing the Internet and capable of providing at least one computer-based program/activity; (d) transmitting the measured electroencephalographic brain activity to said central server via the Internet by way of the computer-based device; (e) providing feedback to the at least one patient in accordance with the measured electroencephalographic brain activity; and (f) receiving a treatment protocol from the central server via the Internet by way of the computer-based device.

In some embodiments, the method includes automatically providing treatment protocols based on the measured electroencephalographic brain activity whereby continued neurofeedback treatments can be performed without monitoring by a therapist.

In some embodiments, the method includes providing neurofeedback treatment, using an automatically generated treatment protocol, simultaneously to at least one of a plurality of patients.

In some embodiments, the method further includes offering for sale a treatment package whereby at least one organization can provide neurofeedback treatment to patients.

In some embodiments, the method further includes offering for sale a treatment package whereby at least one patient can receive neurofeedback treatment.

In some embodiments, the neurofeedback system has a number of applications that run under Microsoft Windows™, which communicate with one another over the Internet and/or another communication network. The information in the system can be saved in a database.

In some embodiments, the neurofeedback system includes a browser based system whose function is to create and manage organizations; clinics; therapists; patients, etc., and manage all of the information and processes for them.

Another portion of the neurofeedback system includes patient features allowing for execution of neurofeedback therapy by an EEG reading from a portable device, which may include provision for connecting to more than one portable device (wherein openness to a number of APIs must be provided); comparison with additional thresholds and parameters that have been determined in the patient treatment protocol and patient feedback (visual/audio, as noted above) depending on whether the patient is meeting the threshold. There is communication that involves the transfer and sending of information between the different portions of the system.

In contrast to US 2010/016753 (Frilik), which discloses the possibility to perform neurofeedback treatment using various devices, the instant system and method provides neurofeedback treatment on any one or more of several computer-based programs/activities, as defined and disclosed herein. In other words, the instant invention provides more than the possibility to use various devices, the instant invention provides for the use of a variety of programs/activities that can be accessed from various devices. These programs/activities include not merely a specially installed, associated or downloaded program/activity, such as associable with a gaming device or video, rather herein the present specification the computer-based programs/activities denote standard computer-loaded or computer accessable programs/activities, best definable by example, to include the Internet (e.g. Internet surfing, on-line games and Youtube); word and presentation processing (e.g. Microsoft Word® and PowerPoint); spreadsheet programs (e.g. Excel); social and professional networking programs (e.g. Facebook®, Twitter®, MySpace, Google+, LinkedIn®); email; and the like; and not merely as provided on various devices. In other words, computer-based programs/activities of the type beyond merely videos and video games, which are presently used.

To help understand the important distinction, the above (additional) programs/activities that are usable for neurofeedback using the instant invention, can be used in there so-called "natural" setting, i.e. using whatever programs/activities the user wishes to use at that time, including switching back and forth between programs/activities. Thus, the instant invention can be used by a patient when using programs/activities including word processing, social network programs, etc., as listed herein.

Further, in contrast to typical current neurofeedback systems, the instant system can serve multiple patients—and while using a variety of computer-based programs/activities.

Certain advantages of the instant system include, but are not necessarily limited to: the system is adapted to work in the patient's natural environment (home, office, etc); the system is relatively inexpensive for the typical patient; the system can be installed remotely; the system has simple hardware (helmet/headset and amplifier) and is wireless; its controller is located in the server and not in the end-user (patient) work station; the system does not require expensive or time consuming diagnosis by a therapist rather the system has a diagnosis mechanism and can produce a treatment protocol automatically; supervision of the treatment by the therapist is not required nor is communication with the patient, which is expensive and there is a shortage of available therapists; the treatment is controllable by a central server whereby treatment results can be saved on the server and analyzed automatically; ongoing changes in the treatment protocol can be performed by the server. Involvement/intervention of a physician reviewing the results is sent/issued in an incorrect report; the treatment can be conveniently performed in the patient's natural computer environment (e.g. while using Facebook or YouTube; Internet surfing; and so on, thereby minimizing or perhaps even eliminating the issue of neurofeedback therapy treatment becoming boring; to ease patients, with ADHD for example, finding it difficult to put themselves in a therapeutic framework, the system has a log or diary system settable by the user and the system can alert the user when to start treatment and to wait to connect to the system's server.

BRIEF DESCRIPTION OF THE DRAWINGS

The present invention will be understood and appreciated more fully from the following detailed description taken in conjunction with the appended drawings in which.

The following detailed description of embodiments of the invention refers to the accompanying drawings referred to above. Dimensions of components and features shown in the figures are chosen for convenience or clarity of presentation and are not necessarily shown to scale. Wherever possible, the same reference numbers will be used throughout the drawings and the following description to refer to the same and like parts.

DETAILED DESCRIPTION OF THE INVENTION

Illustrative embodiments of the invention are described below. In the interest of clarity, not all features/components of an actual implementation are necessarily described.

Figure 1:
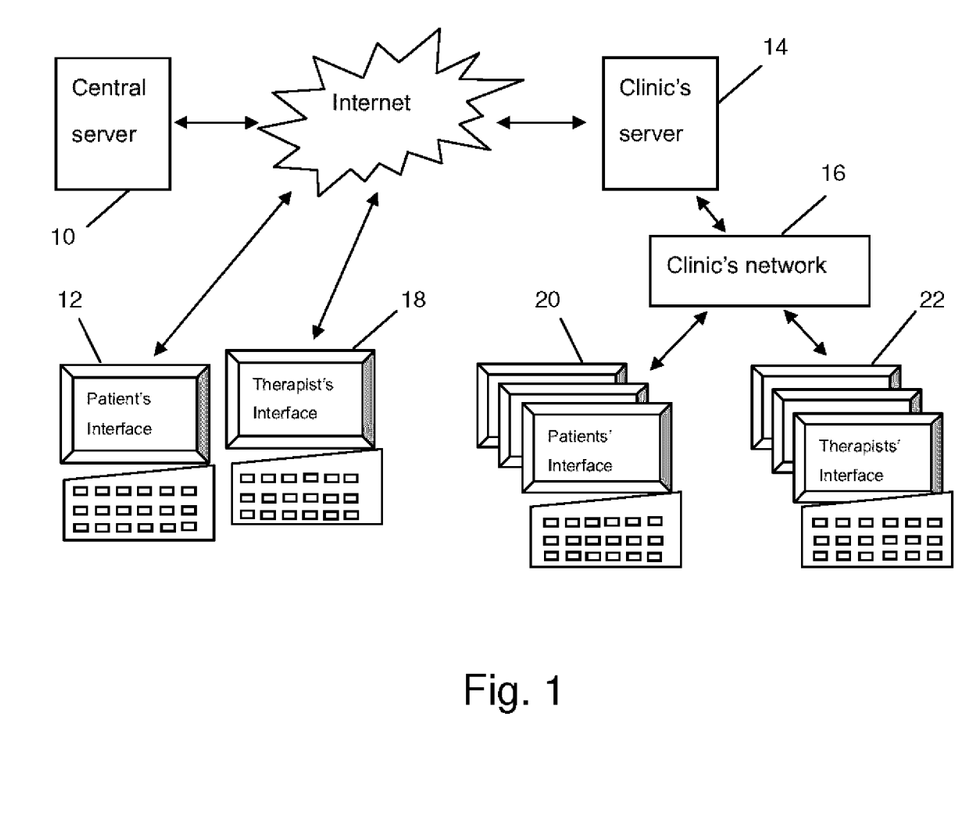
FIG. 1 is a schematic view of an embodiment of a neuropathy/neurofeedback treatment system of the present invention.

FIG. 1 shows an embodiment of a neurofeedback system of the present invention. The system includes a central server 10 and a data collection module 12 operably/communicatively associated with the patient's computer-based device (e.g. desktop computer, laptop computer, smartphone, etc.). Data collection module 12 is configured to receive electroencephalography data associated with the patient. Although described in the singular, there may be several computer-based devices (and thus, several data collection modules 12) for each patient and devices of several patients. The system further includes a clinic's server 14 and clinic's network 16. The users may connect to the network via the Internet. Therapists can also access the system using a therapist's computer-based device 18 via the Internet. Using patients' computer-based devices 20, patients can also access the system via the clinic's network 16; and using therapist's computer-based devices 22, therapists can also access the system via the clinic's network 16.

Via their computer-based device(s), users/patients can connect to central server 10 and after an authorization process they may update and view the relevant data (in accordance with the authorization granted). The system has a number of user types (patient, therapist, clinic, etc.) that have different access authorizations for performing operations.

The neurofeedback central server computer system is designed to manage a number of organizations. An organization consists of a number of clinics (branches of the organization). The head organization or controlling company is the main organization in the system. The authorized parties of the head organization are able, as necessary, to open new organizations in the system and these organizations will purchase treatment packages, for which in some embodiments the system includes a treatment package purchase module. Each organization can consist of one or more clinics. After an organization finishes the purchase of a number of treatment packages, it can allocate treatments to the various clinics that are under it. In addition, the organizations can have patients who work from home. These patients will purchase the treatments from the organizations to which they belong and the accounting will be between the organization and the head organization for the purchase of treatments.

Each clinic has therapists who perform scheduling and tracking of treatments of patients in the clinic. The therapists can update a patient's test protocol. In addition, therapists can generate questionnaires, assign them to patients and receive the answers for updating the therapeutic process. When the patient/user is working (e.g. at home or other "natural" setting/environment) the therapist automatically receives the treatment results. If the therapist decides to change the treatment protocol for the patient, as soon as the patient connects to the Internet, the new treatment protocol will download to the patient's computer based device and will become active in the treatment (i.e. automatically).

The patients put an EEG reader device, such as a head set or individual electrodes on their heads, as known per se, and using a patient application that is installed on the patient's home computer (or other appropriate computer-based device), can perform a treatment procedure and schedule additional treatments. In some embodiments, the headset will be adapted so that it can be hidden by a frontal cap or hat that will allow the patient to roam outside the house without looking strange.

Therapists using the system will typically be identified by a unique identity user number and password, each user number referring to a specific user. Each user will be assigned to a user group in which the authorizations will be set. A user may be assigned to more than one user group. For example, if the therapist is self-employed, he or she will be an organization manager, clinic manager and therapist alike. The following groups will be set in the system:

| Name of group | General description of authorizations for the group |
| --- | --- |
| Company organization managers | General information settings<br>Organization setup and management<br>Clinic setup and management<br>Setup of users for all of the workers in the organization<br>Reports |
| Organization managers | Clinic setup and management<br>Setup of users at the organization level and lower<br>Reports |
| Clinic managers | Setup of users at the clinic level<br>Therapist management<br>Reports |
| Therapist | Accompaniment of patients in the therapeutic process<br>Reports |
| Patient | Execution of actions at the patient level (such as answering questionnaires, start/end of treatment, others) |

The system is preferably set up so that employees of one organization cannot view data of another organization; so that each practitioner may observe or edit (where permitted) only the data that has been created for his/her patients at the clinic or home practice; and the manager of a certain employee will have access to all of the information of the employee (practitioner's patients) and will have at least the same level of authorization for his information Typically, the computer-based devices used will have a browser that supports the HTML5 protocol (such as Internet Explorer 9; Firefox 7; Chrome 14 and more updated versions thereof, or the like. The personal computers (or the like) of the patients typically should have installed Windows XP and .net 4 environment, or more updated versions. Because the system that is installed at the clinics requires high availability, a local environment in the community should be set up to prevent downtime if/when the connection to the Internet fails. The management and control system will typically also be installed externally on the Internet and on internal servers at the clinic.

The Internet server(s) will typically be located in Microsoft's cloud environment, or the equivalent. The server will be allocated the appropriate resources as necessary, for the quantity of use, volume, etc. If necessary, more servers may be added and additional sites created in various countries as supported by the Microsoft cloud. The dispersal of the system at different sites in the world will allow for improvement of performance for users from the same area in the world and in addition will allow for high availability/ survivability if for any reason a certain cite becomes unavailable.

The server(s) on the internal network will be installed on the LAN of the computer network at the clinic. The operating system on the servers is typically Windows 2008 R2 or a more updated version or equivalent. The server specification shall be in accordance with industry standards and should be defined in advance in accordance with the clinic's potential use volume. In accordance with the level of use, the system servers may be separated from the database at the clinic. Exemplary supported operating systems include IOS-5; -Android Ginger Bread/Ice Cream Sandwich; and Windows Mobile 8.

The database on the Internet will typically be Microsoft Azure SQL, which is the database in Microsoft's computing cloud, or a more advanced version or equivalent. The database on the internal network at the clinic will be MS SQL Server 2008 R2, or a more advanced version or equivalent. Initial installation of an express version for reducing the initial setup costs may be performed/occur. Preferably, no database will be installed on the patient's personal computer or equivalent. Use will typically be made of a persistent caching mechanism for sending all of the relevant patient data on the local computer for supporting offline work.

To help ensure security, passwords should be saved on the database in an encrypted manner. The user management mechanism should be Microsoft Asp.net membership provide and role provider, which supports the common security mechanisms of access, identification and verification authorizations (or an updated version or equivalent). A log should be made for each record that has been added/modified or deleted, including who performed the change and at what date it was performed. Because the information system is located on the Internet and contains a number of systems that interface with it (e.g., the patient application, synchronization of the data in from the clinics to the cloud), it is very important to verify the requests that arrive in order to prevent the theft of information or its display and analysis by unauthorized parties. For this purpose, OAuth or an equivalent may be used, which is a common protocol on the Internet for verification and identification of end applications that connect to the system's API. The protocol will be implemented over the Application Programming Interface (API) layer of the management system.

Regarding backup and restoration, the clinic's computer users can define manual or automatic processes that will back up the local database. The database that is in the cloud will be backed up using the automatic tools in the cloud.

The system can be designed, for example, to operate in the Microsoft cloud computing environment (Azure) and internally at the various clinics. The meaning of cloud computing is the receipt of computer resources, such as data processing, information storage, messaging and databases, from a source that is outside the company. The software is typically developed in a high level language in accordance with the common standards in the industry (e.g., C#, ASP, .NET, etc.). The management system can be written using ASP.NET MCV 4 technology (or an equivalent), which is browser based technology.

The elements of the management system in the cloud are as follows:

(1) A user interface element contains all of the processes and all of the screens in the management system.

(2) API (Application Programming Interface)—an element that will provide for access/viewing/update/deletion of the information in the system in accordance with authorizations The elements of the clinic management system are as follows:

1. User interface element—identical to the management system element in the cloud.

2. API—identical to the management element in the cloud.

3. Cloud Synchronization—an element for synchronizing information between the data at the clinic site and the data in the cloud.

4. API Proxy—an element that is responsible for accessing the API of the management system at the clinic and the API of the management system in the cloud using the Cloud Synchronization.

The patient application will be written, for example, in C# .NET 4. The application will be sent as a combination of the operating system service (Windows service) and a Windows application that will be developed, for example, in WinForm or WPF, which will allow the user to command and control the treatment and through rapid access for opening the browser to the management system.

Figure 2:
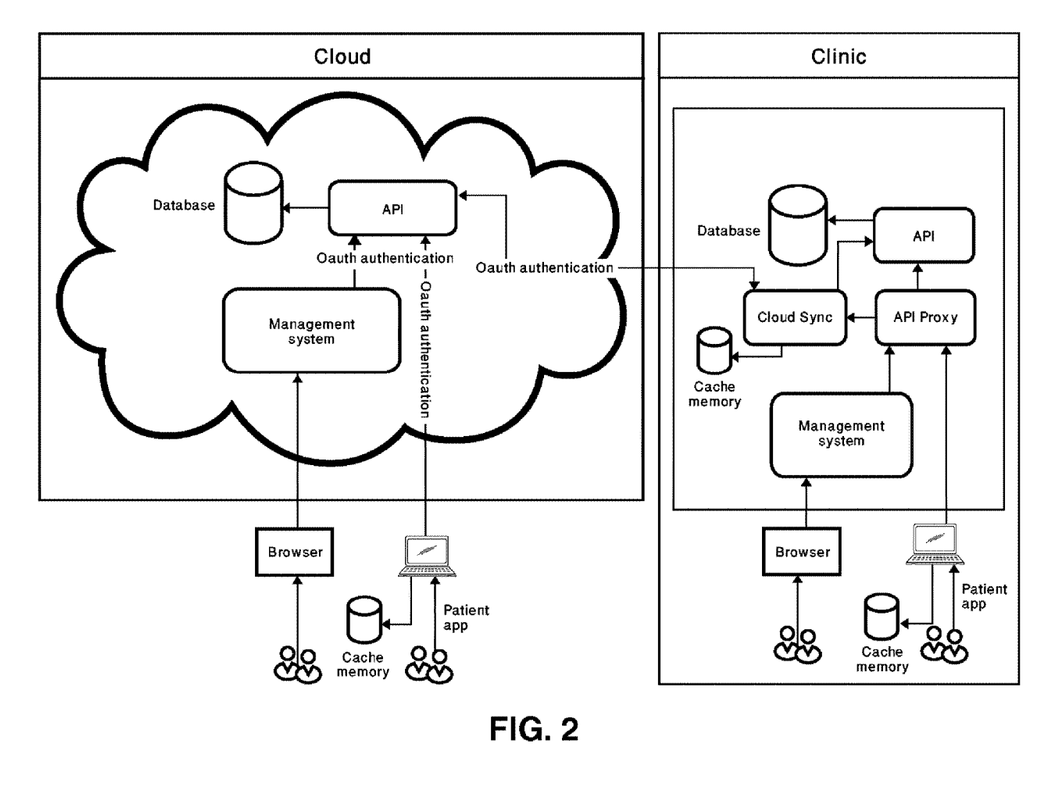
FIG. 2 is a schematic illustrating an exemplary system architecture showing various system environments/structures.

FIG. 2 schematically illustrates an exemplary system architecture, which helps in understanding the various environments/structures of the system.

The Patient application that is installed at home versus the patient application that is installed at the clinic is now explained by way of the following:

The Patient application that is installed at home will require access to the system by entering an identity number and password.

The Patient application that is installed at the clinic will provide access to the system by entering a username and password of the therapist followed by selection of the current patient using the patient finding screen.

The Patient application that is installed at home will not allow real time viewing during the treatment.

The Patient application that is installed at the clinic will allow real time viewing during the treatment.

The Patient application that is installed at home will allow for the setup of a treatment session log for the patient The Patient application installed at home will allow for purchasing of patient treatments (via a patient treatment purchase module of the system).

The Patient application installed at the clinic will not allow for the purchase of treatments for the patient.

The management system installed at the clinic compared to the management system installed on the cloud:

The management system installed on the cloud will provide for creation/changing of organizations, clinics and users.

The management system that is installed at the clinic will not allow for creation/changing of organizations and will allow for creation/change of clinics, patients and not of other user types.

The management system at the clinic will contain only the data that is relevant to the organization to which the clinic belongs The management system in the cloud will contain all of the data of all existing organizations The management system that is installed at the clinic will display a link that will provide for opening of a browser for the management system on the cloud.

Interfaces:

As part of the management system, there is an access interface to the management system's information. The interface may be written, for example, using ASP.NET WEB API technology. The technology allows for creation of an API whose data consumption is small with regard to data volume and is easy to use with regard to the end applications that connect to it. The technology is intended for the consumption of services from one central system by each application that is written in any technology, such as client applications, mobile applications and Web applications.

The API will include the following applications:
(a) The management system itself
(b) The Patient application
(c) The Cloud Synchronization service that is responsible for the transfer of information from the clinic to the cloud As set forth, the information system will be installed at each clinic that asks to use the system, even when there is no communication to the Internet. In addition, the system will typically be installed in one central place on the cloud. In order to synchronize the information between the Clinic's databases and the central database, the synchronization will be performed using a specialized module developed to synchronize the information.

Interface to the EEG reader: An interface based on the API of existing neurofeedback hardware systems may be supported. Other interfaces to additional devices can be added to the system and the patient may chose a desired device. The interface can be written using, for example, Microsoft Extensions Framework (MEF) technology in order to give the option of adding interfaces to additional EEG readers without need for rewriting the patient application. The interface may be based, for example, on serial communication (38.4 k rate, 8 bit, 1 stop bit, without parity) in a 4 byte format, with, for example, the following structure:

| Bits | B7 | B6 | B5 | B4 | B3 | B2 | B1 | B0 |
|---|---|---|---|---|---|---|---|---|
| Signal | 0 | 0 | 1 = Low Battery | Resolution = Fixed 11 (12 ... 16 bits) | | Sampling Rate 000 = 122, 001 = 128, 010 = 256, 011 = 512 | | |
| ALC 1 | 0 | 1 | | Auto Level Control Gain Channel 1 | | | | |
| Status | 1 | 0 | 1 = Right Button Pressed | 1 = Left Button Pressed | Not Used | 1 = Channel2 OK | 1 = Channel1 OK | |
| ALC 2 | 1 | 1 | | Auto Level Control Gain Channel 2 | | | | |

The calculation of the signal voltage (Peek-to-Peek) can be performed using the following formula:

$$\text{Output } Vp\text{-}p = ([12b \text{ value}]/4096) * 185.5 uVpp * (63-X)/24$$

Where X is a constant 39; and Value is a number consisting of 12 bits gathered in 4 consecutive frames.

Example (C++) of an implementation of the synchronization is shown below:

```
while (flgDevice_Synchronised == false)
{
   lblSyncStatus->Caption = "Sync Search...";
   Synchronised_Status_Hold = false ;
   Sync_Search_Buffer [ Sync_Search_Buffer_pntr ] =
   (Buffer[k] & 0xC0) ;
```

-continued

```
    if (( Sync_Search_Buffer_pntr - Packet_Size ) < 0 )
        Temp01 = Sync_Search_Buffer_pntr + Packet_Size
;
    else
        Temp01 = Sync_Search_Buffer_pntr - Packet_Size ; //
to account for circular buffer
    if (((Sync_Search_Buffer[Temp01] + 0x40) & 0xC0 ) ==
        (Sync_Search_Buffer[Sync_Search_Buffer_pntr]))
        {    // if sync bit match, then...
            if (Sync_Test_Result[Sync_Test_Result_pntr ] >
2) // hits required to "sync"
        {
            Sync_Test_Result[0] = Sync_Test_Result[1]
= Sync_Test_Result[2]
                = Sync_Test_Result[3] =
Sync_Test_Result[4] = Sync_Test_Result[5]
                = Sync_Test_Result[6] =
Sync_Test_Result[7] = Sync_Test_Result[8]
                = Sync_Test_Result[9] = 0 ;
            Sync_Byte_Current = Sync_Search_Buffer[
Temp01 ] ;
            flgDevice_Synchronised = true ;
            Packet_Sync_Marker = 0 ;
            tmrSampleBurst->Enabled = true ;
            if ( Synchronised_Status_Hold == false )
            {
                Synchronised_Status_Hold = true ;
                lblSyncStatus->Caption =
"Synchronized" ;
            }
            break ; // jump to synchronized
processing
        }
        else
            Sync_Test_Result[Sync_Test_Result_pntr]++
;
        }
    else   // no sync match
        Sync_Test_Result[Sync_Test_Result_pntr] = 0 ;
```

Regarding synchronization of data between clinics and the Cloud system, because there is a need for constant availability of the system within the clinic, in some embodiments, a set up a separate environment of the system at each clinic can be obtained by those clinics desiring such. The data that is saved at the clinic level should be synchronized and saved in the central database of the system as well as in the cloud, and alternatively, all of the actions that are performed directly with the cloud system that are related to a certain clinic should be synchronized and saved in the personal database of that clinic.

Synchronization of this type, assuming that there are many clinics, can be a complicated process that is expensive in time and resources and therefore this using this option should consider these issues.

In addition, because the system is located in clinics of various organizations in addition to the company organization and a separate database is managed for it that the IT team of the clinic will have access to, it is necessary to develop advanced identification mechanisms that will allow for synchronization from the server in the cloud only of the information that is relevant and in addition completed regardless of anything that is related to the setup and management of user profiles in the personal database of the clinic. For example, a profile of the clinic manager must not be allowed to be modified directly in the personal database of the clinic from a clinic manager to a company organization manager, which loophole would allow him full access to all of the data in the system in the cloud.

Each clinic will receive a verification that is unique to it (using the OAuth protocol for example), which will provide for identification of the clinic in the cloud and allow for synchronization of the appropriate data. In the database in the clinic, all of the relevant data of the organization to which it is assigned will be synchronized (because there are entities such as questionnaires and protocols that are managed at the organization level) including the user profiles of all users in the organization.

The synchronization of the information between the clinic and the cloud will transfer only the new or updated information and not all of the information anew. In order to identify changes in records for the synchronization, a mechanism that saves information for each record such as when it was created and by who and when it was updated and by who can be added in some embodiments. In some embodiments, each time a change is made in a record, the timestamp will be updated in accordance with the change made. In some embodiments, during each synchronization, a check will be made of each required record whether the information is more updated than the current record.

For preventing errors in the synchronization, the fields of the creating and updating user will not be linked to the user table (i.e. there will be no foreign key) in order to prevent the situation of a record arriving for synchronization at a certain clinic and the user record that updated it not existing at the clinic (for example the record was created by a company organization manager).

During the synchronization for each record, in some embodiments, a check will be made as to whether the record exists. If it does, the data in it will be overwritten by the data that arrives from the synchronization and not from the record that will be created.

In addition, in some embodiments, in order not to harm the integrity of the data, records will be deleted virtually only, i.e. each table will have a column titled 'Deleted?' added to it and when a record is deleted, that record will not be deleted from the database but the value in the 'Deleted?' field will change to 'Yes'.

Because there is data that is synchronized from different clinics and there is also data that is updated directly in the central system in the cloud, the record key should preferably an identifier number plus the code of the branch that created the record (the branch code will be 0 if the record was created in the cloud).

The order of synchronization of the tables will be from the highest server to the layer underneath in order to prevent a clash in editing records from two layers in the same time.

An exemplary synchronization process is as follows:

Synchronization from the Clinic to the System in the Cloud

In order to save resources an ensure that the database in the cloud is almost always updated with all of the information that is input in the clinics, any action that is performed inside the clinic will be saved immediately both in the local database at the clinic and in the database in the cloud. The synchronization is performed by developing an API Proxy element, with which the management systems and the Patient application will both work. During the execution of an operation, the API Proxy element will transfer the information in a synchronous manner to the local database using the local API element) and in addition will forward an asynchronous request to the Cloud Sync element.

When there is communication with the Internet, the information that reaches the Cloud Synchronization will be transferred directly to the cloud by secure access to the API element of the system in the cloud. It is assumed that nearly all of the time, except in extraordinary cases, there will be communication with the Internet.

If/when the communication with the Internet fails, the information concerning the Cloud Synchronization will be saved in the Cloud Synchronization cash memory element. A scheduling process will be run that will sample the communication every few minutes and if there is communication, the information will be sent as a batch file of updates.

The batch file will contain a script of all of the updates that have been made based on their chronological order. The batch file that will be sent to the cloud will enter the update queue. This queue will have all of the updates from all of the different clinics sent to it. The system in the cloud will run the scripts from all of the files according to the order of entry to the queue The batch file will have a hash code of the data from that file added to it so that it may be made sure that the file that is received on the server side is received in full. If for any reason the file does not pass in full or there was a failure in sending, a resending mechanism will be applied that will try to send the file 5 times more. If the transfer fails, a warning will be sent to the system administrator. No file will be sent from the clinic to the cloud before the preceding file is successfully sent in order to make sure that the data in the cloud is valid.

Clash (contention) management—if certain records that arrive from different clinics, or that were updated in the cloud itself, clash with the records that came from other sources, the last record that is input will take precedence.

To reduce the state of unavailability of data input service from the various clinics in the cloud, the batch file will not be more than half a megabyte in size. If there is data exceeding this volume, a number of batch files of smaller volumes will be created.

No change of user profiles will be sent to the cloud except for those of patients. This means that after initial synchronization, a user may have different passwords in the internal system (the user profiles are read only in the internal system). All of the user management, addition/update, assignment of function, etc., will be carried out with the system in the cloud. The aim of this restriction is to prevent impersonation or an attempt to get access at a higher level to the central system.

The system in the clinic will make a communication check with the system in the cloud once a day, or at time periods set or decided upon by the system manager. If for about two weeks there is no communication between the clinic system and the cloud system, a message will be sent to the manager for the company organization, for preventing fraud and reducing the risk of an independent organization disconnecting from the system in the cloud and working independently without the need to pay the company organization.

Synchronization from the Cloud to the Clinic

The synchronization data will be executed in pull form rather than in push form, meaning that any system that is installed in any clinic will request its updates and the information will not arrive at the initiative of the system to the cloud. This restriction is intended to prevent a problem of availability and a need for expensive resources in the cloud. If there are many clinics in the world, and the synchronization is performed by push to the different clinics, the synchronization is a very heavy process. In addition, this architecture will facilitate the settings at the IT level of the various clinics (there is no need for a constant IP, firewall settings, etc.).

The Cloud Sync service that is at the various clinics will perform a check every fifteen minutes, or at time periods set or decided upon by the system manager, for updates for the clinic. If there are updates (and as a result, if this is the initial synchronization for that clinic), a positive answer will return with a key code for a batch file that will be created at the site (because the file can contain many records, the process is performed in an asynchronous manner). The Cloud Sync service will sample once a minute whether the batch file has been created, and assuming that it has been created, will download the file locally.

The batch file comes with a hash code of the file content in order to check that the file has arrived in full. If for any reason the file does not pass in full or there was a failure in receiving, a repeat receipt mechanism will be applied that will try to download the file five times more. If the transfer fails, a warning will be sent to the system administrator.

To reduce the unavailability of the file downloading service, the download will be performed in lots of up to half a megabyte per lot. If any error occurs on the side of the system in the cloud in producing the batch file, a warning will be sent to the system administrator. If the Cloud Sync service does not locate the batch file in the system in the cloud for more than five minutes, a warning will be sent to the system administrator.

Because more than one update request may be received from more than one clinic at any given time, the process in the cloud system will generate the files concurrently in accordance with the resources of the servers in the cloud.

If between the test of the Cloud Sync and the receipt of the batch file with the updates, any updates are made in the system in the cloud that are related to the clinic requesting the information, this data will not be transferred in the batch file being generated but in the following update. If the update of the data from the batch file in the system in the clinic fails for any reason, any future synchronization process will be neutralized and a warning will be sent to the system administrator. Additional updates will not be checked by the Cloud Sync service until the successful end of the current update in the system.

The synchronization from the cloud to the clinic will only be performed when there is no data that is waiting for synchronization to the cloud.

Exemplary Interface Between the Management System and the Patient System in the Organization Because a therapist is able to see the cycle of the treatment that is occurring at the clinic in real time and update protocol data concerning it, there is a need for a real time interface (e.g. therapist interface) with the treatment application. This option is not relevant in the connection of a patient from home.

1. The communication will be performed using sockets in P2P configuration.

2. Because the communication is performed at the personal computer (patient/client), a Silverlight element will be developed in the management system that will connect by opening a socket directly to the patient's computer.

3. In the Silverlight elements, the relevant graphs will be shown and a change in the protocol will be made possible (e.g., via a "bridge" between the HTML code and the Silverlight element).

4. During the start of a new treatment session in the Patient application in the clinic, the IP address of the patient's computer will be sent to the clinic server.

5. When the patient logs into the current treatment management screen, the IP address of the patient's computer will be retrieved and a direct channel will be opened to his computer.

6. Once the treatment session is over, the IP record will be deleted from the database.

Exemplary Interface Between the Management System in the Cloud and the Patient System at Home (1) When the patient logs in for the first time at home to the patient application, the system will download from the database in the cloud all the relevant patient data into a local cache memory file.

(2) If there is no communication, the system will allow for offline login and for treatments to be performed.

(3) At the end of each treatment session, the system will try to transfer the treatment results to the cloud. If there is no communication, the system will sample the network once an hour, or at time periods set or decided upon by the system manager, and when the communication returns, the system will send the data created.

(4) At the beginning of each treatment, if there is communication, the system will import current data on the protocol and the current questionnaire of the user.

Exemplary system screens: The screens noted herein below are an example only for orientation and do not represent the UI or the graphic design that may be implemented. The purpose of the screens is to illustrate which fields and actions will be made possible in the screens and what the information flow between the different screens is.

- To view details on the business processes related to each screen, see the business characterization of the system.
- Mandatory fields are indicated by an asterisk (*) next to each field name.
- For tables in the different screens, the data will have a funnel (▽)icon next to the columns that provide for filtering. Filtering allows for reducing the items in the list in accordance with the value entered in the filter.
- The possible expressions in the filtration of text type columns are: "Contains" and "Equals to".
- The possible expressions in the filtration of number type columns are: "Equal to", "Is greater than" and "Is less than".
- The screens appearing in this document for the various entities appear in the format of updating/addition (text and selection boxes for fields). However, these screens must also be considered in viewing mode. In viewing mode, the data will appear as text in a column, without the ability to update the information, without the relevant buttons for updating, etc.
- As a rule, each data table in the various screens, if relevant, will have a viewing mode for the items in the table.
- In the authorization table for each page, the mark * indicates that the authorization is only for the data that the user created or that was created for him.
- In the authorization table for each page. The mark ** indicates that the authorization is only for the data that the user created or other users at his level created (for example an item that was created by one therapist in the organization may be edited by all therapists in that same organization).

Multiple languages:
- The user interface will be written in a manner that provides for its conversion into other languages.
- The user's language will be determined by the definition in the organization to which the user is linked.
- The initial language in which the user interface will be written will be English.
- Use will be made of the multi-language mechanism of asp.net to create user interface languages, i.e. for each language, a file (Resource resx) will be set up to save all of the texts in that particular language. The user's language will be chosen by the locale (language region) chosen by the organization. In addition, for displaying code tables, the database will have the relevant translations of each entry in the code table defined.

Functionality checks
- Identity card number—will require a check digit to be entered. A check will be made for the legality of the identity card number.
- Integers—a check will be made to ensure that the text entered is an integer.
- Decimal numbers—a check will be made to ensure that the text entered is an integer or decimal.
- Telephone—the system will perform a check for the legality of the telephone number
- Dates—a check will be made to ensure that the date is legal in the format that is defined for that country
- Email—a check will be made to ensure that the email format is valid
- Length—for each text field, a check will be made to ensure that the field length is not greater than the field length defined in the database Sorts
- The selection boxes in the various system screens will be sorted alphabetically in ascending order.
- The tables in the system will be sorted by default according to their title/name column alphabetically in ascending order. The system will allow the user to establish a different column for sorting and also change the sort order from ascending to descending order.

Display
- Decimal numbers will be shown up to 2 digits after the decimal point. If the number that is entered is an integer, the decimal part of the number will not be shown (e.g. the number 32 will not be displayed as 32.00)
- In text fields, unnecessary spaces will be removed if they exist before and after the text.
- For each numerical field, an identifier of the information type will be displayed (for example, a value representing percent will be appended by the '%' sign, for a value representing seconds, the 's' sign will be appended and so on).
- For table type fields, the numeric information type identifier will be displayed in the column titles in the table and not for the value itself (for example, in the protocol table, the success threshold column name will be "Success threshold (%)" and the values in the table will appear without the '%' sign).

Access to the system screens will be enabled according to authorizations. Screens that users have no access to will not be displayed to those users. In addition, the system will determined for the user upon accessing a certain screen whether he/she has authorization to update/delete information in addition to viewing authorization.

Exemplary authentication: When logging into the system, the initial screen will be the authentication screen that will ask the user for his email address and password. To facilitate the administration process for the system administrator, a user will not be locked after multiple failed login attempts.

After about ten erroneous trials, an email message will be sent to the system administrator to warn of a possible hacking attempt. When logging into the system. The home page will be determined in accordance with the authorizations of the user.

Because there are differences in functionality between the system installed in the cloud and the system installed at the clinic, the access page of the system installed at the clinic will have a link shown to the system installed in the cloud so that there will be an option for directly accessing the system in the cloud.

Purchase of treatments: Via the system, treatments can be purchased from the head organization by a sub-organization, typically via the system in the cloud. In some embodiments, an organization may allocate (without purchasing) treatments between the different clinics of the same organization. A patient (e.g. who works from home) may purchase treatments from the organization to which he is assigned. The purchase by a patient will add a treatment allocation record to a treatment allocation list for the patient within the organization.

An organization/clinic/patient may see how many treatments remain and receive a warning by email and on their home page if they have only a few treatments left (in accordance with the system parameter settings). Purchase of treatments by a patient will not detract from the number of treatments of the organization.

Typically, the system will include the capacity to receive or provide information via various displays (e.g. computer screens). Such "screens" may include one or more of the following: treatment protocol configuration screens, where one may view, edit (e.g. change a "success threshold" or a threshold calculation) or create a new protocol; a screen indicating electrode placement and/o the number of electrodes to be used; a patient questionnaire screen intended to provide various clinics a template or example for producing their own questionnaires; organization screens to keep track of sub-organizations under the company organization; a treatment purchase screen, available to clinics and patients; a synchronization screen to allow a system administrator at the clinic to view the status of synchronizations between the clinic servers and the system in the cloud; a screen displaying a list of all of the clinics that are assigned to the organization; a user-configuration screen for configuring all types of users in the system (e.g. organizational users, clinics, therapists, patients); a treatment history screen for viewing the treatment history of a particular patient; a patient management screen; a patient evaluation screen, which can typically provide patient results data and graphs; a patient log screen for keeping track of the frequency and timing of treatments; a data retrieval screen, which can include one or more a search fields for looking up a patient's records; a patient profile screen for the patient to enter his/her details such as name, sex, age, address, etc.; a patient treatment history, treatment log and results screen(s) for keeping track of patient activity and results—and which may also keep track of which therapist(s) are involved with the patient and electrode location. The also system typically includes protocol screens or templates and/or tables to help the therapists.

One or more of the above-mentioned screens, or portions thereof, may be read only type screens/portions.

In some embodiments, the system is adapted to evaluate patient questionnaires to suggest/provide treatment protocols.

Typically, the database of the management system in the cloud and the database of the management system at a clinic is basically the same except for a number of differences that may exist because of the different purpose of the environment.

Reports: The system can also be adapted to facilitate reports, such as, patient treatment progress reports, e.g. including progress measured in terms of the amplitude level of the brain waves (channel frequency levels—alpha, beta, theta, delta, SMR) analyzed, and other patient reports such as relating to treatment schedule (session dates) and so on; patient progress reports via questionnaires; clinic progress reports; and organization level reports.

In summary/reiterating, the present system is a neurofeedback trainer that is on the one hand simple, on the other hand has the ability to train the patient to on how to use the patient's personal computer at home (or other computer based device) for the treatment with a minimum of installations/downloading and definitions.

Once installed, the system typically "requires" the patient to perform the exercise (treatment) at times determined by the patient in advance. The patient sets a schedule of the days and the hours (time of day) of appropriate treatment. System will require a weekly quota of hours of treatment (unless specific dates were indicated as free time). The treatment schedule is set by the care manager, who could be: the patient (if mature/adult), a professional (therapist), a parent or other care-giver.

The treatment schedule is based on a calendar mechanism that allows treatment according to a schedule that is preset by the patient and/or the therapist/clinician. Once a required treatment appears on the user's screen (e.g. via an icon), informing him/her of the possibility for treatment, the treatment will begin with the consent of the patient, for example by pressing a start button. This procedure will cause the application to provide treatment for a time period preset by the clinician and/or automatically by creation of a treatment at a treatment center. The system will also allow manual operation/actuation of the treatment, for those who so choose, and will define that the treatment is not controlled by a (predetermined) schedule.

In the case of a system failure the system can automatically report the issue or allow sending a message to a support center and the company organization's customer service that will help the patient to solve the problem.

In some embodiments, the system alerts the patient's computer based device to start treatment. Schedule checking will require the patient to attach electrodes (e.g. via a training helmet). In some embodiments, if the patient has not performed the required task, the system will not allow work on the computer based device.

It is a key feature of the present system that the training can be performed in the natural environment of the patient. For example, browsing the Web, using office software, e-mailing, using Facebook chat, playing on-line computer games, etc.

The system will provide feedback (disturbance) to the patient typically by blurring, twitching/shaking, darkening, fading out or changing the background color of the work screen, or changing font characteristics if the screen contains reading material, or the like, in response to the electrical activity of the brain, measured during treatment (in other words, when the patient does not meet the therapy/treatment goal as defined in the therapy/treatment protocol as determined by the system or therapist). Alternatively, the system can provide feedback to the patient by playing sounds while the patient is busy doing other things at home, such as reading a book. As the distance/difference from the target result increases, the screen feedback disturbance will increase; and vice versa (the closer the patient is to meeting the desired treatment protocol value(s) the less will be the feedback disturbance, i.e. the more normal the screen display will become.

At the end of the treatment, the system will stop the operation, store the information collected/accumulated in the treatment and diminish one treatment of the accumulated treatments acquired from the patient and then will send the information through the wireless network to the company organization center.

The system hardware and software typically includes the following components:

1. An EEG headset, with electrodes, to be worn on the patient's head.

2. Amplifiers, typically directly connected or integral to the headset, for amplifying reception of electrical signals attached to the head set.

3. A hardware component that converts the information received from the electrodes to a digital signal transmitted to a computer for processing.

4. Software that allows a suitable response regarding each of the programs in which the patient works and reacts according to the signals received from the head set.

5. Software that manages the treatment and comprises/is adapted to provide: quantitative analysis; mathematical algorithms based on Fourier transformation or similar, or other suitable algorithms that disassembles/analyses the electrical signal according to frequency; comparison with treatment protocol (treatment protocol is also a mathematical algorithm) set for each patient; a software unit communicating with screen control software.

6. A therapist screen in a separate window that allows viewing an EEG during treatment and allows controlling the difficulty level. This screen can be used or blocked by the care manager.

The instant invention provides for remote control neurofeedback treatment (automatic/computer therapist). Further, in contrast to the present situation, which typically requires the physical presence of a therapist the system, or at least the use of limited "vehicles" for treatment (e.g. videos, computer games), the instant invention allows for automatic treatment protocols, remote monitoring, and the use of computer-based programs/activities" in addition to videos and computer console-type games, as currently used.

This concept can be thought of a treatment route in the patient's natural (non-clinic and non-video or computer console game) setting, for example at home, work or while travelling; and, the treatment can be administered and supervised without a "human" therapist. Regardless, the instant invention allows for expert human intervention performed by the system administrator, for example, in case the system has identified a situation indicating the need for such intervention.

In that regard, the system will allow a therapist to manage a follow-up file for each of the therapist's patients, to perform assessments and manually set treatment protocol or automatically set treatment protocol by the system, according to the therapist's choice. The therapist will have be screen control available that will allow viewing the EEG and view the achievements of the patient during treatment. The screen control will allow the therapist to control the difficulty level of the treatment and to change the protocol during the treatment. In this regard, the system is adapted to provide a positive reinforcement for progress over time.

The present system can provide an initial assessment of the patient; and create automatic treatment protocols, based on assessment data received and analyzed by the system, for each treatment; and allow treatment to be offered to patients with a variety of neurological problems and psychological issues. Also, the instant invention enables treatment in a care clinic, under the supervision of a professional therapist or the use of an automatically provided protocol that is built by the system that can be loaded from the main server to the patient at the initial stage of each treatment before beginning a treatment session.

The system, whether used in a clinic or in the patient's natural environment, will typically send reports on an assessment performed at the beginning of each training (treatment session) and a reporting on the learning graph/curve during the treatment session and between treatments. The therapist can manually intervene and change and produce protocol values, or can let the system generate the protocol at the beginning, according to the choice of the therapist. In this case, the updated protocol will be loaded into the system located with the patient at the initial stage for each treatment session, before the session begins.

Evaluation (Assessment) by the System:

In some preferred embodiments, the system: a) checks the electrical activity of the patient and calculate a number of parameters of this electrical activity—and the parameters that will be considered will be based both on the relationship between the various frequencies of different brain regions and of the absolute values and relative values measured; b) checks various correlations existing between the electrical activity in one location relative to the electrical activity in another location; c) evaluates the various synchronization processes that occur during the EEG signal; d) calculates the properties of the electrical activity both at rest and while the patient performs tasks such as reading, writing, drawing, performing calculations and the like; e) requests that the patient fills out questionnaires, or performs computerized neuropsychology tests (that are known/exist and standard in the field presently) to assess the problem from which the patient suffers; f) performs a diagnosis for each individual/patient based on the main complaints of the patient.

Automatic Construction of a Therapeutic Protocol for the Treatment of Various Neuropsychiatric Disorders In some preferred embodiments, with consideration of the overall calculations performed by the system, each patient will have a suitable treatment protocol. The protocol will be based on the entirety of the data collected from the patient and the known scientific treatment information at the time. Building the therapeutic protocol will be based on consideration all of the data in different weights and offers a treatment protocol.

The system based on three layers. The lowest layer is the patient screen. This screen is installed on the patient's/client's computer. This patient screen layer is influenced by the patients EEG and displays the feedback, as well as records the treatment session.

The clinic layer is the next layer and creates or updates a protocol, builds or updates a questionnaire and has the ability to change a threshold, on-line, for treatment in the clinic.

The central/main server holds the database of all clinics & patients. It is able to automatically decide & build a protocol on the base of an automatic assessment. The automatic system can maintain the threshold of an end patient without a clinician interference.

The central/main server will allow the user(s), i.e. clinician/therapist and/or patients, to receive service (connect with the system) wherever they are via the Internet in order to allow them to connect from anywhere in the world to receive the service required.

The presence of the central/main server simplifies the installation of the software at the therapist or at the patient; and simplifies updating the software, which may be performed from time to time. In some embodiments, the central/main server includes software components and customer service and billing/invoicing (billing the patient or therapist). The central/main system will store all the information obtained from endpoints and patients and save the information as a structure entities.

The central/main server will contain the code that all the components of the system will use so that performing a treatment will require loading from the central/main system.

Scenarios: As noted, a main objective of the system is that it can be integrated in the daily life of the patient, including using a computer based devise such as a mobile device, for example, a laptop computer, Smartphone/cellphone, Tablet/iPad or the like, via programming/activities computer-based programs/activities detailed above.

A first stage of achieving that objective is based on the use of a computer-based device, as defined above. The work environment is typically a Windows-based laptop or desktop regardless of the activity performed on it. The response is obtainable using any software on which one works while training.

In a second stage, the system is combined or associated with the mobile device. The procedure is performed using an application written specifically for the computer-based activity, for example for Facebook where the user can get a reaction as part of a game that is integrated in the Facebook world fit in the style of Farmvil. The source of the software can be from so-called "application" stores provided by various suppliers.

It should be understood that the above description is merely exemplary and that there are various embodiments of the present invention that may be devised, mutatis mutandis, and that the features described in the above-described embodiments, and those not described herein, may be used separately or in any suitable combination; and the invention can be devised in accordance with embodiments not necessarily described above.

What is claimed is:

1. A neurofeedback system for providing neurofeedback treatment to at least one patient comprising:
    at least one sensor removably attached to the head of the at least one patient and configured to measure electroencephalographic brain activity of the at least one patient;
    a central server connected to a network and configured to store at least one treatment protocol algorithm whereby the central server provides at least one treatment protocol using feedback from the measured electroencephalographic brain activity;
    at least one data collection module operable in a computer-based device;
    said computer-based device having a network connection whereby said computer-based device provides communication between said network and said at least one data collection module;
    said at least one sensor adapted to transmit said electroencephalographic brain activity to said at least one data collection module and then to said network;
    said at least one data collection module configured to:
        (a) transmit the measured electroencephalographic brain activity to said central server via said network;
        (b) provide feedback to the at least one patient in accordance with the measured electroencephalographic brain activity; and
        (c) receive said treatment protocol from the central server via said network; and
    a computer output device in electrical communication with said computer-based device;
    wherein said at least one data collection module is further configured such that, during the neurofeedback treatment, the module accesses any user-selectable computer-based program/activity and said computer output device is configured to provide the feedback to the at least one patient by modifying an output of said user-selectable computer-based program/activity in response to said electroencephalographic brain activity, said user-selectable computer-based programs/activities include any available computer-based programs/activities that comprise any and all of the following: word processing programs; spreadsheet programs; presentation programs; social networking programs; online games; e-mail systems; Internet surfing; computer apps; and video-sharing programs/sites, all of which being selectable by the at least one patient and independent from said neurofeedback system.

2. The system of claim 1, further comprising at least one therapist interface for respectively interfacing with at least one therapist and interfacing with said network to thereby receive said electroencephalographic brain activity data measured by said at least one sensor.

3. The system of claim 1, further comprising a clinic server configured to interface with said network.

4. The system of claim 1, wherein the central server is configured to automatically provide said at least one treatment protocol based on the electroencephalographic brain activity whereby continued neurofeedback treatments can be performed without monitoring by a therapist.

5. The system of claim 1, wherein the computer-based device includes any one or combination of a desk-top computer; a laptop computer; a Personal Digital Assistant; a cellphone / smartphone; and a computer operated gaming device.

6. The system of claim 1, comprising a plurality of data collection modules whereby a plurality of patients can simultaneously use the system.

7. The system of claim 1, further comprising a treatment package purchase module for allowing an organization to purchase use of the system.

8. The system of claim 1, further comprising a patient treatment purchase module for allowing at least one patient to purchase one or more neurofeedback treatments.

9. The system of claim 1, wherein the at least one treatment protocol received via said network includes at least one subsequent treatment protocol in accordance with progress of the at least one patient.

10. The system of claim 1, wherein said feedback to each patient is an audio feedback.

11. The system of claim 1, wherein said feedback to each patient is a visual feedback.

12. The system of claim 1, wherein said at least one sensor is part of a portable head-set.

13. A method of providing neurofeedback treatment to at least one patient, the method comprising:
    securing electrodes to the head of the at least one patient, the electrodes configured to measure electroencephalographic brain activity;
    providing a central server connected to a network and configured to store at least one treatment protocol algorithm whereby the central server provides at least one treatment protocol using the measured electroencephalographic brain activity;
    loading at least one data collection module operable in a computer-based device, said computer-based device having a network connection whereby said computer-based device provides communication between said network and said at least one data collection module;

said at least one data collection module is connected to said network using said computer-based device;

the at least one data collection module accessing any user-selectable computer-based program/activity during the neurofeedback treatment wherein the computer-based program/activity comprises any and all of the following: word processing programs; spreadsheet programs; presentation programs; social networking programs; on-line games; e-mail systems; Internet surfing; and video-sharing programs/sites, all of which being selectable by the at least one patient and independent from said neurofeedback system;

transmitting the measured electroencephalographic brain activity to said central server via said network;

providing feedback to the at least one patient in accordance with the measured electroencephalographic brain activity; and receiving said at least one treatment protocol from the central server via said network; and providing a computer output device in electrical communication with said computer-based device and configured to provide the feedback to the at least one patient by modifying an output of said user-selectable computer-based program/activity in response to said electroencephalographic brain activity.

14. The method of claim 13, comprising automatically providing said at least one treatment protocol based on the measured electroencephalographic brain activity whereby continued neurofeedback treatments can be performed without monitoring by a therapist.

15. The method of claim 13, comprising providing neurofeedback treatment to a plurality of patients, simultaneously.

16. The method of claim 13, comprising providing neurofeedback treatment, using an automatically generated treatment protocol, simultaneously to at least one of a plurality of patients.

17. The method of claim 13, further comprising offering for sale a treatment package purchase module whereby at least one organization can provide neurofeedback treatment to patients.

18. The method of claim 13, further comprising offering for sale a treatment package whereby at least one patient can receive neurofeedback treatment.

* * * * *